United States Patent [19]
Fugoso et al.

[11] Patent Number: 5,643,209
[45] Date of Patent: Jul. 1, 1997

[54] HIGH PRESSURE BALLOON TIP

[75] Inventors: Mauricio Lintag Fugoso, Chula Vista; Candida Naguit Figueroa, San Diego, both of Calif.

[73] Assignee: Medtronic, Inc., Minneapolis, Minn.

[21] Appl. No.: 572,908

[22] Filed: Dec. 15, 1995

[51] Int. Cl.⁶ ............................................. A61M 29/00
[52] U.S. Cl. ............................ 604/96; 606/194; 604/103
[58] Field of Search ............................... 606/192, 194; 604/103, 264, 280–284, 96

[56] References Cited

U.S. PATENT DOCUMENTS

| | | | |
|---|---|---|---|
| 4,702,252 | 10/1987 | Brooks et al. | 128/344 |
| 4,739,768 | 4/1988 | Engelson | 128/658 |
| 4,787,388 | 11/1988 | Hofman | 128/344 |
| 4,798,586 | 1/1989 | Stevens | 604/96 |
| 4,820,349 | 4/1989 | Saab | 128/344 |
| 4,921,483 | 5/1990 | Wijay et al. | 604/96 |
| 5,047,045 | 9/1991 | Arney et al. | 606/194 |
| 5,209,728 | 5/1993 | Kraus et al. | 604/96 |
| 5,290,230 | 3/1994 | Ainsworth et al. | 604/96 |
| 5,338,295 | 8/1994 | Cornelius et al. | 604/96 |
| 5,411,016 | 5/1995 | Kume et al. | 128/6 |
| 5,423,771 | 6/1995 | Imran | 604/281 |
| B1 4,739,768 | 11/1994 | Engelson | 128/658 |

Primary Examiner—John D. Yasko
Assistant Examiner—Cris L. Rodriguez
Attorney, Agent, or Firm—Dianne M. F. Plunkett; Harold R. Patton

[57] ABSTRACT

The present invention is accomplished by providing a dilatation balloon catheter with a flexible tip comprising a catheter body having proximal and distal ends with an outer shaft defining an inflation lumen. The catheter body has a coaxial inner guidewire shaft defining a guidewire lumen. An inflatable balloon is mounted at the distal end of the catheter body, the balloon has an outer diameter, an inner diameter, a distal end and a proximal end. The proximal end of the balloon is in fluid communication with the distal end of the inflation lumen and the distal end of the balloon is sealingly mounted to the guidewire shaft. The guidewire shaft extends distal to the distal end of the balloon, the guidewire shaft has an outer diameter and a step down area. The guidewire shaft Step down area begins just proximal to the distal end of the balloon. The guidewire shaft step down area has an outer diameter which is less than the outer diameter of the guidewire shaft. The distal end of the balloon is adhesively bonded to the guidewire shaft. The adhesive begins proximal to the distal end of the balloon and fills between the inner diameter of the balloon and the outer diameter of the guidewire shaft. The adhesive extends distally from the height of the outer diameter of the balloon at the distal end of the balloon. The adhesive tapers down distally to the outer diameter of the guidewire shaft step down area not more than 1 mm proximal of the distal end of the guidewire shaft.

8 Claims, 2 Drawing Sheets

HIGH PRESSURE BALLOON TIP

FIELD OF THE INVENTION

The present invention relates to angioplasty catheters, and more particularly, to high pressure balloon tips.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The original catheter can then be withdrawn and a catheter of a different size or another device such as an atherectomy device can be inserted.

The design of medical devices for insertion into body organs has always involved trading off various performance characteristics in the design of a satisfactory implement. PTCA requires a device which is stiff enough to be pushable and go through blockage, while being flexible enough to go around bends. Dilatation balloon catheters commonly have a guidewire lumen pass through the balloon with the balloon and guidewire lumen being bonded at the distal end. This makes the tip of the dilatation catheter a relatively rigid structure which is desired for pushing the dilatation balloon catheter through a stenosis or blocked artery. If the tip of the catheter is too stiff, however, it may not be able to navigate sharp turns to get to the stenosis. This limits the effectiveness of the dilatation balloon catheter to arteries within easy reach of the heart.

Conventional angioplasty balloons fall into high, medium and low pressure ranges. Low pressure balloons are those which fall into rated burst pressures below 6 atm. Medium pressure balloons are those which fall into rated burst pressures between 6 and 12 atm. High pressure balloons are those which fall into rated burst pressures above 12 atm. Burst pressure is determined by such factors as wall thickness and tensile strength.

High pressure balloons are desirable because they have the ability to exert more force and crack hard lesions. High pressure balloons are useful in stent deployment. A stent is a half-inch stainless-steel or tantalum mesh sleeve that props open blocked coronary arteries, keeping them from reclosing after balloon angioplasty. A balloon of appropriate size and pressure is first used to open the lesion. The process is repeated with a stent crimped on a high pressure balloon. The stent is deployed when the balloon is inflated. The stent remains as a permanent scaffold after the balloon is withdrawn. A high pressure balloon is necessary for stent deployment because the stent must be forced against the artery's interior wall so that it will fully expand thereby precluding the ends of the stent from hanging down into the channel encouraging the formation of thrombus.

High pressure balloon materials are stiffer than conventional materials. Whereas conventional balloons use materials such as polyethylene, high pressure balloons use materials such as polyethylene terephthalate (PET) or Nylon 12. When high pressure balloon materials are used, the balloon tip can become too stiff and will not negotiate tortuous paths as well as more compliant conventional balloons.

Copending commonly held U.S. Ser. No. 08/312,359 to Ma for "Catheter Flexible Tip" discloses a flexible tip formed from balloon material distally extending beyond the guidewire lumen, the inner diameter of the flexible tip generally equal to the inner diameter of the guidewire lumen.

U.S. Pat. No. 4,739,768 to Engelson for "Catheter for Guide-Wire Tracking" discloses a drug delivery catheter with a relatively stiff proximal segment and a relatively flexible distal segment that is at least 5 cm long. It can be advanced along a guidewire placed in a tortuous vascular path and provides a method for delivery of an injectable fluid at a tissue site. While the distal segment itself may be very flexible and works well for drug delivery, it is too long and flexible to push through a blockage in the artery or stenosis.

In Ma and Engelson the balloon material extends beyond the inner lumen thereby forming the balloon tip. Using high pressure balloon materials for such a tip design yields a tip which is too stiff.

SUMMARY OF THE INVENTION

It is an object of the invention to provide a flexible tip design using high pressure balloon material. Such a structure would provide the needed pushability and force transmission in the tip area to push through blockage in the artery while being flexible enough to navigate the tortuous path and sharp curves through small arteries. The above features and advantages of the present invention as well as others, are accomplished by providing a dilatation balloon catheter with a flexible tip comprising a catheter body having proximal and distal ends with an outer shaft defining an inflation lumen. The catheter body has a coaxial inner guidewire shaft defining a guidewire lumen. An inflatable balloon is mounted at the distal end of the catheter body, the balloon has an outer diameter, an inner diameter, a distal end and a proximal end. The proximal end of the balloon is in fluid communication with the distal end of the inflation lumen and the distal end of the balloon is sealingly mounted to the guidewire shaft. The guidewire shaft extends distal to the distal end of the balloon, the guidewire shaft has an outer diameter and a step down area. The guidewire shaft step down area begins just proximal to the distal end of the balloon. The guidewire shaft step down area has an outer diameter which is less than the outer diameter of the guidewire shaft. The distal end of the balloon is adhesively bonded to the guidewire shaft. The adhesive begins proximal to the distal end of the balloon and fills between the inner diameter of the balloon and the outer diameter of the guidewire shaft. The adhesive extends distally from the height of the outer diameter of the balloon at the distal end of the balloon. The adhesive tapers down distally to the outer diameter of the guidewire shaft step down area not more than 1 mm proximal of the distal end of the guidewire shaft.

DETAILED DESCRIPTION OF THE PREFERRED EMBODIMENTS

Applicant's balloon tip design can be used with high pressure balloon materials such as PET and PET blend materials although other high pressure balloon materials would be suitable. Desirable materials should have minimum balloon diameter growth up to the rated burst pressure as well as better rewrap. The balloon tip design can be used for a variety of applications such as stent deployment or drug delivery.

The standard balloon size for coronary artery applications ranges from 5 mm to 50 mm in length with counterpart balloon diameters ranging from 1.5 mm to 5.0 mm in quarter sizes typically. The minimum rated burst pressure applicant seeks to achieve is 16–18 arm with an average rated burst pressure of at least 20–22 atm. Nominal balloon pressure should be 6 arm with compliance in quarter size diameter growth from 6 atm to 16 atm.

Figure 1:
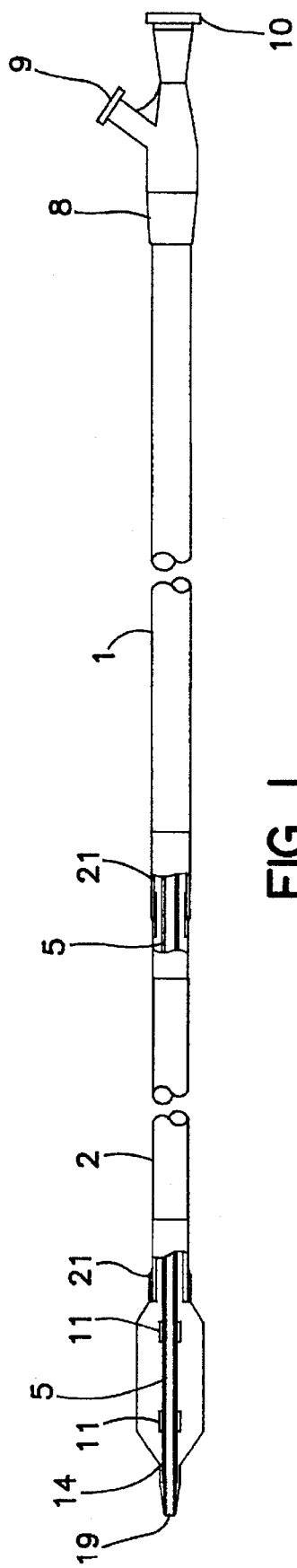
FIG. 1 is a longitudinal view of a catheter with a high pressure balloon tip.

FIG. 1 is a longitudinal view of a high pressure balloon catheter with a co-axial design adapted for use in percutaneous transluminal coronary angioplasty (PTCA). The proximal shaft 1 can be made of polyimide. This increases stiffness with reduced wall thickness and contributes to reduced inflation/deflation times. The distal shaft 2 can be made of 50% high density polyethylene (HDPE) and 50% low density polyethylene (LDPE). The distal shaft 2 is designed to handle 500 plus psi pressure and still remain flexible enough to navigate tortuous paths. The guidewire shaft can be made of HDPE. The distal end of the proximal shaft 1 overlaps the proximal end of the distal shaft 2. The proximal end of distal shaft 2 has a step down 7 to receive the distal end of proximal shaft 1. The step down 7 minimizes the transition in outer diameter from the proximal shaft 1 to the distal shaft 2. This is held together by cyanoacrylate adhesive 20 (shaded area), as for example, Loctite black spot super bonder adhesive. FIG. 1 shows how the proximal end of the proximal shaft 1 and the proximal end of the guidewire shaft 5 are affixed to the manifold 8 so that the proximal shaft 1 is in fluid communication with the inflation/deflation port 9 via the inflection lumen 21. The guidewire shaft 5 is in fluid communication with the guidewire port 10.

Figure 2:
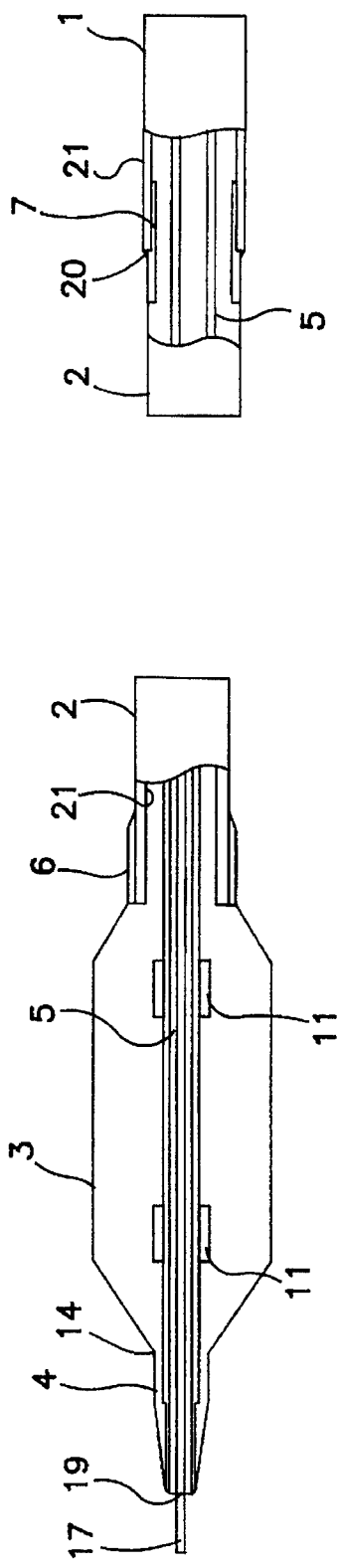
FIG. 2 is an enlargement of the balloon of FIG. 1.

FIG. 2 is a cross-sectional view of the balloon 3 portion. The marker bands 11 are made of two radiopaque tabular tubes bonded with cyanoacrylate adhesive. These can be made of platinum material of approximately 1.5 mm in length and are positioned approximately 0.5 mm from the balloon cones and bonded with cyanoacrylate adhesive on the guidewire shaft 5. The balloon proximal tail 6 is approximately 3 mm in length and is bonded with ultraviolet curable adhesive such as Loctite 3321 to the distal end of distal shaft 2.

Figure 3:
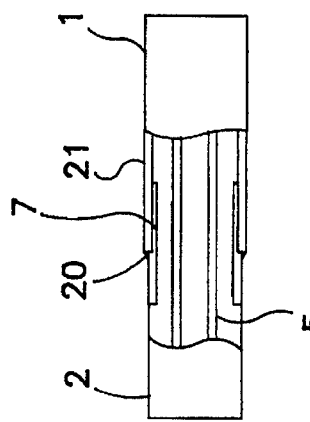
FIG. 3 is the cross sectional view of the distal shaft of FIG. 1.

FIG. 3 represents the cross sectional view of the distal shaft 2 of FIG. 1. The polyimide proximal shaft 1 is approximately 110 cm in length with an outer diameter of 3.2 french and a wall thickness of 0.003 inches. The distal shaft 2 has a length of 27 cm, an outer diameter of 2.9 french and a wall thickness of 0.003 inches. The proximal end of the distal shaft 2 is formed to create a step 7 of approximately 3 mm to 5 mm in length. The step 7 is sufficiently deep to yield a reduced outer diameter which mates with the inner diameter of the proximal shaft 1. When a 3.2 french proximal shaft 1 is mated with a 2.9 french distal shaft 2 the depth of the step must be approximately 0.003 mm. The step 7 fits the inner diameter of the distal end of the proximal shaft 1 and is bonded with Loctite super bonder 420 adhesive. The 3.2 french size proximal shaft 1 and 2.9 size distal shaft 2 have been chosen because they optimize a flexible distal shaft 2 for tracking with a proximal shaft 1 size that permits an optimal industry standard deflation time for balloons with a length of 2 cm to 4 cm. A larger distal shaft 2 will yield a stiffer product while a smaller proximal shaft 1 will yield a longer deflation time.

Figure 4:
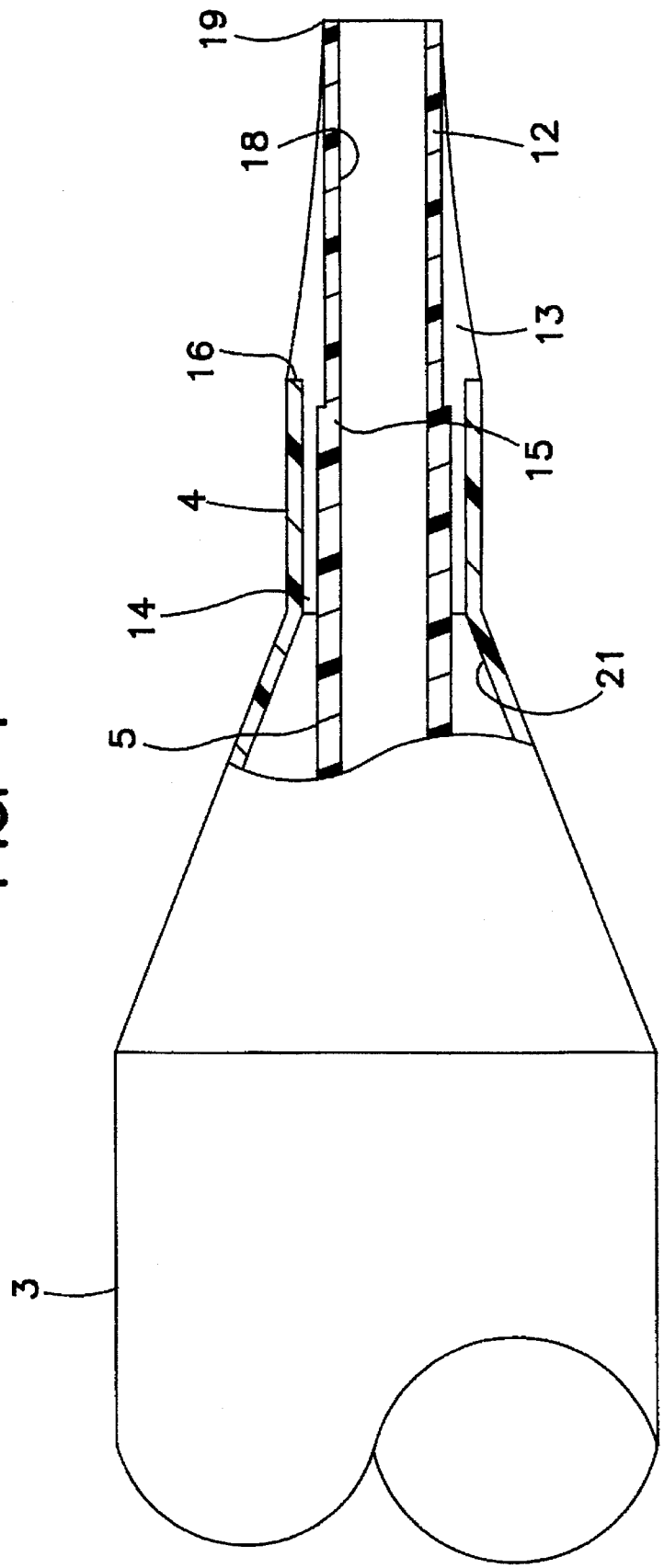
FIG. 4 is the cross-sectional view of the distal tip design of FIG. 1.

FIG. 4 is a cross-sectional enlargement of the distal tip design. The guidewire shaft 5 has a radiused distal end and a step down at transition 15. The outer diameter of the guidewire shaft 5 before transition 15 is 0.023 inches. The outer diameter of stepped down guidewire shaft 12 after transition 15 is 0.020 inches. The length of the stepped down guidewire shaft 12 after the transition 15 is approximately 3.5 mm. The length from the balloon distal tip 16 to guidewire shaft distal tip 19 can range from 2 mm to 5 mm. The stepped down transition 15 begins 0.5 mm to 1.0 mm proximal to the distal end of the balloon distal tip 16. The balloon distal tail 4 extends approximately 1 mm to 2 mm from the distal end of the balloon cone 14. This length was chosen for the distal tail 4 so as to minimize the stiff section of the balloon distal end yet provide enough area to enable the adhesive bond to withstand the high pressure.

The adhesive bond 13 is created as follows. Beginning at approximately the balloon cone distal end 14, the inner surface of the balloon distal tail 4 is bonded 13 (shaded area) to the outer surface of the guidewire shaft 5 including the step down portion 12. A flexible, fast curing, ultraviolet adhesive such as Loctite 3321 may be used. The adhesive bond 13 continues as a filler beyond the balloon distal tip 16 and gradually tapers distally to the same diameter as the outer diameter of the guidewire shaft step down portion 12 anywhere between 1 mm proximal to the distal tip 19 and to the distal tip 19. Tapering off the adhesive bond 13 not more than 1 mm proximal to the distal tip 19 provides greater flexibility and better tracking. The adhesive can be injected and manually smoothed and tapered with a hypodermic needle. Those skilled in the art would recognize that the adhesive could also be molded. Molding with a rubber mold is more expensive, however, as the mold cannot be reused after the adhesive cures.

The adhesively bonded step down design provides more tip flexibility at the distal end of the catheter. It also prevents kinking and buckling by providing more support for the guidewire lumen when the tip is subjected to compression and bending.

The method of creating the step down portion 12 of guidewire shaft 5 is as follows. A mandrel with a diameter of approximately 0.016 inches and a length of 4.0 inches is inserted into one end of the guidewire lumen 18 for support. This mandrel supported portion of the guidewire shaft 5 is then inserted (drawn) into a heated die with an inner diameter of between 0.0195 inches to 0.020 inches thus creating the step down portion 12.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 1 | Proximal Shaft |
| 2 | Distal Shaft |
| 3 | Balloon |
| 4 | Balloon Distal Tail |
| 5 | Guidewire Shaft |
| 6 | Balloon Proximal Tail |
| 7 | Step |
| 8 | Manifold |

-continued

| No. | Component |
| --- | --- |
| 9 | Inflation/Deflation Port |
| 10 | Guidewire Port |
| 11 | Marker Band |
| 12 | Guidewire Step Down Portion |
| 13 | Bond |
| 14 | Balloon Cone Distal End |
| 15 | Transition |
| 16 | Balloon Distal Tip |
| 17 | Guidewire |
| 18 | Guidewire Lumen |
| 19 | Guidewire Shaft Distal Tip |
| 20 | Adhesive |
| 21 | inflation Lumen |

What is claimed is:

1. A dilatation balloon catheter with a flexible tip comprising:

a catheter body having proximal and distal ends with an outer shaft defining an inflation lumen;

the catheter body having a coaxial inner guidewire shaft defining a guidewire lumen;

the guidewire shaft having a distal tip;

an inflatable balloon mounted at the distal end of the catheter body, the balloon having an outer diameter and an inner diameter, a proximal cone end and a distal cone end extending into a distal tip, a distal end and a proximal end, the proximal end of the balloon in fluid communication with the distal end of the inflation lumen and the distal end of the balloon sealingly mounted to the guidewire shaft;

the guidewire shaft extending distal to the distal end of the balloon, the guidewire shaft having an outer diameter and a step down area, the guidewire shaft step down area beginning distal to the distal end of a balloon cone distal end, the guidewire shaft step down area having an outer diameter which is less than the outer diameter of the guidewire shaft; and the distal end of the balloon being bonded to the guidewire shaft with an adhesive, the adhesive beginning proximal to the distal end of the balloon and filling between the inner diameter of the balloon and the outer diameter of the guidewire shaft, the adhesive extending distally from the height of the outer diameter of the balloon at the distal end of the balloon, the adhesive tapering down distally to the outer diameter of the guidewire shaft step down area not more than 1 mm proximal of the distal end of the guidewire shaft.

2. A catheter according to claim 1 wherein the depth of the step down area is approximately 0.003 ram.

3. A catheter according to claim 1 wherein the length of the step down area between the balloon distal tip and the guidewire shaft distal tip ranges between approximately 2 mm and 5 mm.

4. A catheter according to claim 1 wherein the guidewire shaft step down area begins approximately 0.5 mm to 1.0 mm proximal to the distal end of the balloon distal tip.

5. A catheter according to claim 1 wherein the adhesive is a flexible, fast curing ultraviolet adhesive.

6. A catheter according to claim 1 wherein the balloon has a distal balloon cone, the distal balloon cone tapering distally until the balloon forms a balloon distal tail continuing parallel with the guidewire shaft.

7. A catheter according to claim 6 wherein the balloon distal tail ranges between approximately 1 mm and 2 mm in length.

8. A catheter according to claim 1 wherein the balloon is formed of material with a rated burst pressure above 12 atm.

* * * * *

UNITED STATES PATENT AND TRADEMARK OFFICE
CERTIFICATE OF CORRECTION

PATENT NO. : 5,643,209
DATED : July 1, 1997
INVENTOR(S) : Fugoso et al.

It is certified that error appears in the above-identified patent and that said Letters Patent is hereby corrected as shown below:

Col. 5, Line 35,        "shalt" should be "shaft"

Col. 6, Line 16,        "0.003 ram." should be "0.003 mm."

Col. 3, Line 10:        "arm" should be "atm"

Col. 3, Line 13:        "arm" should be "atm"

Col 3, Line 35:        "9 via the inflection lumen 21" should be "9 via the inflation lumen 21"

Col. 5, Line 16:        "inflation Lumen" should be "Inflation Lumen"

Abstract, line 14,        "Step" should be "step"

Signed and Sealed this

Nineteenth Day of May, 1998

*Attest:*

BRUCE LEHMAN

*Attesting Officer*      *Commissioner of Patents and Trademarks*